(12) United States Patent
Liu

(10) Patent No.: US 7,912,174 B2
(45) Date of Patent: Mar. 22, 2011

(54) COMPUTED TOMOGRAPHY SYSTEM AND METHOD

(75) Inventor: Tong Liu, Singapore (SG)

(73) Assignee: Agency For Science, Technology and Research, Centros (SG)

(*) Notice: Subject to any disclaimer, the term of this patent is extended or adjusted under 35 U.S.C. 154(b) by 265 days.

(21) Appl. No.: 12/089,885

(22) PCT Filed: Oct. 13, 2005

(86) PCT No.: PCT/SG2005/000354
§ 371 (c)(1),
(2), (4) Date: Apr. 10, 2008

(87) PCT Pub. No.: WO2007/043974
PCT Pub. Date: Apr. 19, 2007

(65) Prior Publication Data
US 2008/0253510 A1      Oct. 16, 2008

(51) Int. Cl.
*A61B 6/03* (2006.01)
(52) U.S. Cl. .................. 378/4; 378/10; 378/19
(58) Field of Classification Search ............ 378/4, 10, 378/19, 20
See application file for complete search history.

(56) References Cited

U.S. PATENT DOCUMENTS
4,703,424 A    10/1987  Gullberg et al.
5,228,071 A *  7/1993   Kamata et al. ............ 378/20

FOREIGN PATENT DOCUMENTS
JP          62284250         12/1987
JP          2004/037267 A    2/2004

OTHER PUBLICATIONS
International Preliminary Report on Patentability dated Apr. 16, 2008 for PCT/SG2005/00354, filed Oct. 13, 2005.

* cited by examiner

*Primary Examiner* — Chih-Cheng G Kao
(74) *Attorney, Agent, or Firm* — Knobbe, Martens, Olson & Bear LLP

(57) ABSTRACT

A computed tomography system having a fixed X-ray source [10] for producing a fan beam [20], a fixed digital detector [12] and a manipulator [14] for holding and rotating an object [16] to be inspected. Left and right projections of the rotated object on the fixed digital detector are used to determine a central ray, reconstruction of an image of the object being based on the central ray position. A corresponding method and apparatus are also disclosed.

18 Claims, 12 Drawing Sheets

| Object name | Pen-Shaped Cap | Walnut | Aluminum Foam | Carved Ceramic Owl |
|---|---|---|---|---|
| Object picture |  |  |  |  |
| Central ray (pixel) | 600.3124 | 601.5844 | 601.0841 | 601.5122 |

COMPUTED TOMOGRAPHY SYSTEM AND METHOD

FIELD OF THE INVENTION

This invention relates to a computed tomography system and method and refers particularly, though not exclusively, to an X-ray computed tomography inspection system and method for industrial application. More particularly, the invention relates to the determination of the central ray by use of projections of the object to be scanned

BACKGROUND OF THE INVENTION

A typical X-ray micro-computed tomography ("CT") system for industrial applications consists of an X-ray source, a manipulator/rotator for positioning and rotating the object to be scanned, and an X-ray detector (camera). A good CT scan requires the accurate determination of the central ray. The central ray is sometimes called the iso-channel and is the virtual projection of the center-of-rotation on the detector.

Most fan-beam micro-CT inspection systems are also equipped with two-dimensional inspection as their basic capability. These systems frequently require that the manipulator move from place-to-place; and that the rotator be mounted on, and removable from, the manipulator. The consequence of this flexibility is the prerequisite determination of the central ray each time the manipulator or the rotator is moved. Even with the same manipulator coordinates, generally the system will give two central ray positions that may be sufficiently different to be unacceptable.

A common solution to this problem is to use a wire phantom to calibrate the central ray position before each CT scan. To do so, the wire phantom is placed on the rotational axis and is rotated for 360 degrees in predetermined angular steps. The projections of the wire phantom at all angles are then recorded and used for the determination of the central ray. The wire phantom is usually quite small so that it can be treated as a point for all angles. With fan-beam geometry, due to the small deviation of the wire phantom to the axis of the rotation, the central ray is simply determined as being center of the sinogram of the wire phantom.

The use of a wire phantom to determine the central ray position creates many problems including, but not limited to: reducing the speed of the CT process; introducing errors when changing the object for the wire phantom due to different weight, different fixing status, and so forth, thereby affecting the final CT image quality; and CT scans cannot be automated. Large errors result when large magnification is needed, and the object has to be placed close to the source. In this case, the manipulator is required to move away from the source so that there is space for changing the object for the wire phantom and vise versa.

SUMMARY OF THE INVENTION

In accordance with a first preferred aspect there is provided a computed tomography system comprising:
(a) a fixed X-ray source for producing a fan beam;
(b) a fixed digital detector;
(c) a manipulator for holding and rotating an object to be inspected;
wherein left and right projections of the rotated object on the fixed digital detector are used to determine a central ray position, reconstruction of an image of the object being based on the central ray position.

According to a second preferred aspect there is provided a computed tomography method comprising:
(a) producing a fan beam of X-rays at a fixed X-ray;
(b) detecting the X-rays at a fixed digital detector;
(c) rotating an object to be inspected using a manipulator;
(d) determining left and right projections of the object on the fixed digital detector;
(e) determining a central ray position from the left and right projections; and
(f) reconstructing an image of the object using the central ray position.

A sinogram of the projections of the object may be used to determine the central ray position. The central ray may be determined by identifying the left and right ends of the sinogram.

An included angle between the left projection of the object, the fixed X-ray source, and the right projection of the object, may be used to determine the central ray. The central ray may bisect the included angle.

A part of the object with a largest radius to an axis of rotation is used to determine the left and right projections of the object on the fixed digital detector, the left projection of the part being a leftmost projection and the right projection being the rightmost projection. Alternatively, the left and right projections of a point of the object which generate a much clearer contrast may be used to determine the central ray position. The point may comprise a relatively small object made of a material more dense than that of the object; the relatively small object being attached to the object. The relatively small object may be attached to the object remote from at least one area of interest of the object for enabling a reconstructed image quality to not be affected.

BRIEF DESCRIPTION OF THE DRAWINGS

In order that the present invention may be fully understood and readily put into practical effect, there shall now be described by way of non-limitative example only preferred embodiments of the present invention, the description being with reference to the accompanying illustrative drawings.

In the drawings.

DETAILED DESCRIPTION OF THE PREFERRED EMBODIMENTS

The CT scan of the object to be inspected is performed over 360 degrees, or over an arc of 180 degrees plus the fan-beam angle, at selected angles. The projections at each angle are recorded. These projections are then used for both central ray determination and image reconstruction. The principle behind the method is that the left end and the right end of the sinogram of a selected object slice come from the point on the object which has the largest radius from the rotation axis of the object. The central ray bisects the angle formed by the two end points and the X-ray source point. Therefore, with prior knowledge of the central channel (which is always fixed) the central ray can be determined by a geometric relationship. The central ray may be determined simply as the center of the left and right ends of the sinogram if high accuracy is not required, or the left and right ends identified are close to each other, or the angles formed by the left projection and right projection with respect to the central channel are both small.

Figure 1A:
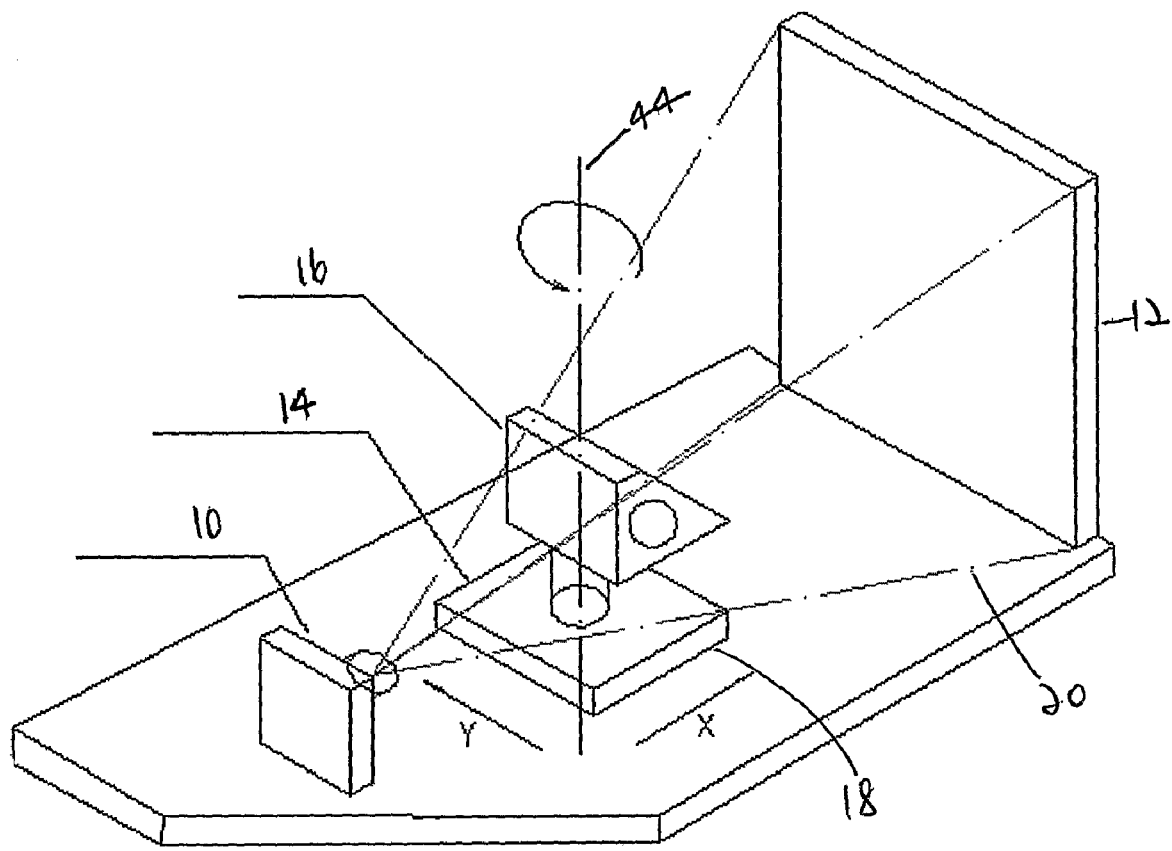
FIG. 1(a) is a schematic representation of a typical prior art X-ray micro-CT system for industrial application.

FIG. 1(a) shows a schematic representation of a typical prior art micro-CT system. It consists of a fixed X-ray source, a fixed flat panel X-ray detector 12 and a manipulator 14 with a rotator 18 for holding, moving and rotating an object 16 to be inspected. The manipulator 14 may be a high precision positioning stage that can move at least in the x, y and/or z directions; and the rotator 18 can rotate about an axis that is aligned to be parallel to one dimension of the detector array. An X-ray fan beam 20 is generated from the X-ray source 10, passing through the object 16 and projecting on the detector 12. The magnification of the system is determined by the source-to-object distance 30 (SOD) (i.e. from 10 to 16) and the source-to-image 32 (SID) distance (i.e. from 10 to 12).

Figure 1B:
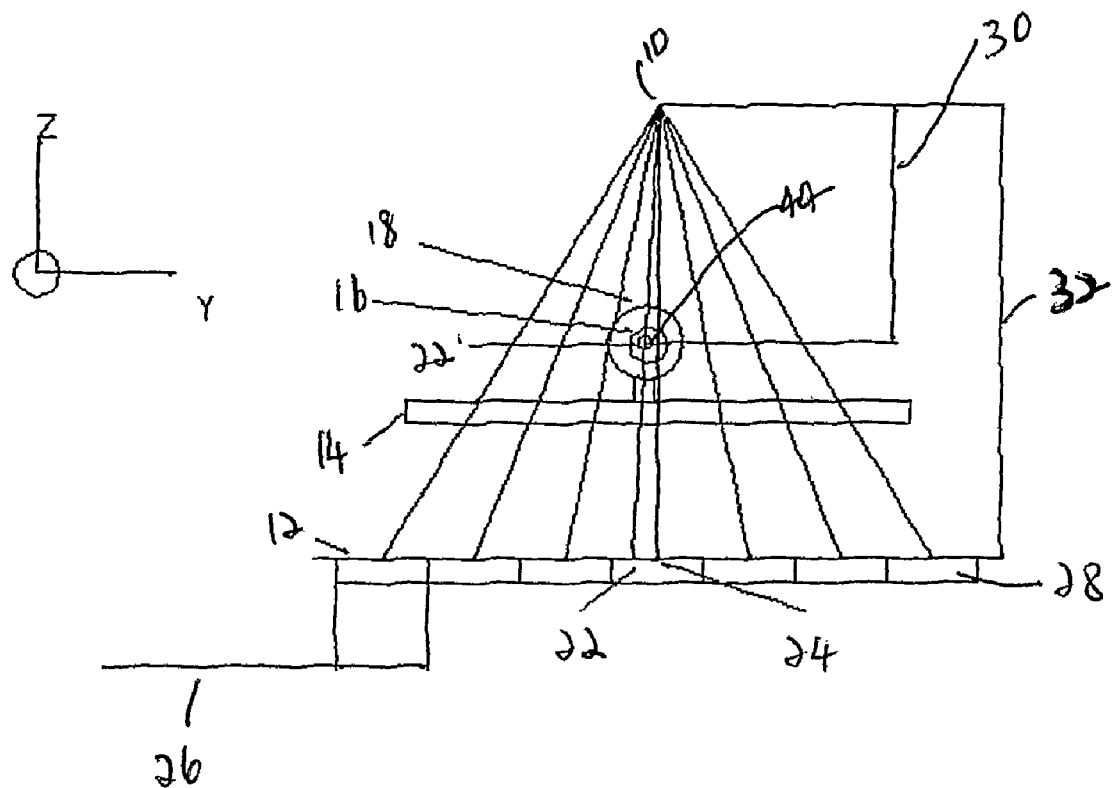
FIG. 1(b) illustrates a prior art CT scan and reconstruction system.

FIG. 1(b) illustrates the arrangement for a CT scan. The central ray (iso-channel) 22 is defined as the projection of the rotation axis 44 on the detector 12. The central channel 24 is the detector cell that the X ray projects on and which is perpendicular to the plane of the detector 12. The pixel size 26 is the size of each cell 28 of detector 12.

Figure 2:
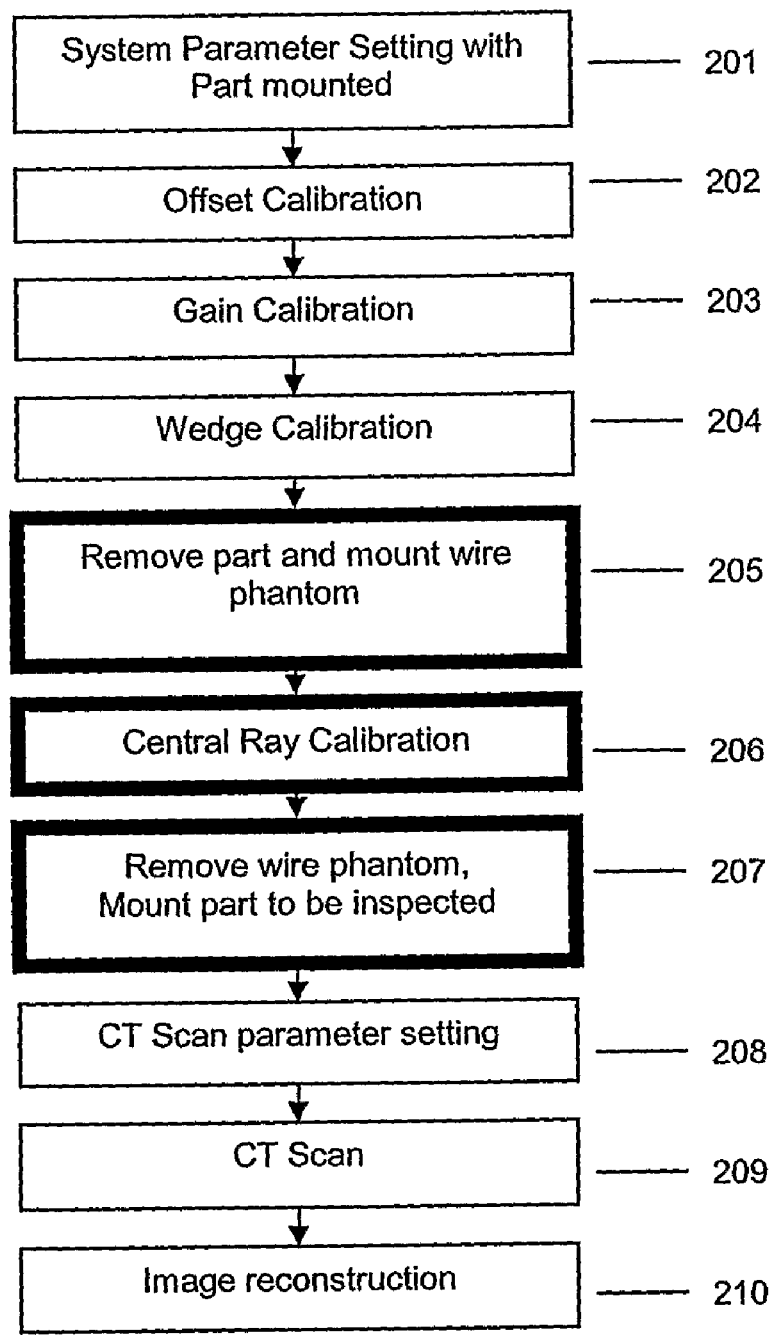
FIG. 2 is a flowchart of a prior art CT scan process with the CT system of FIGS. 1(a) and 1(b)
Figure 3A:
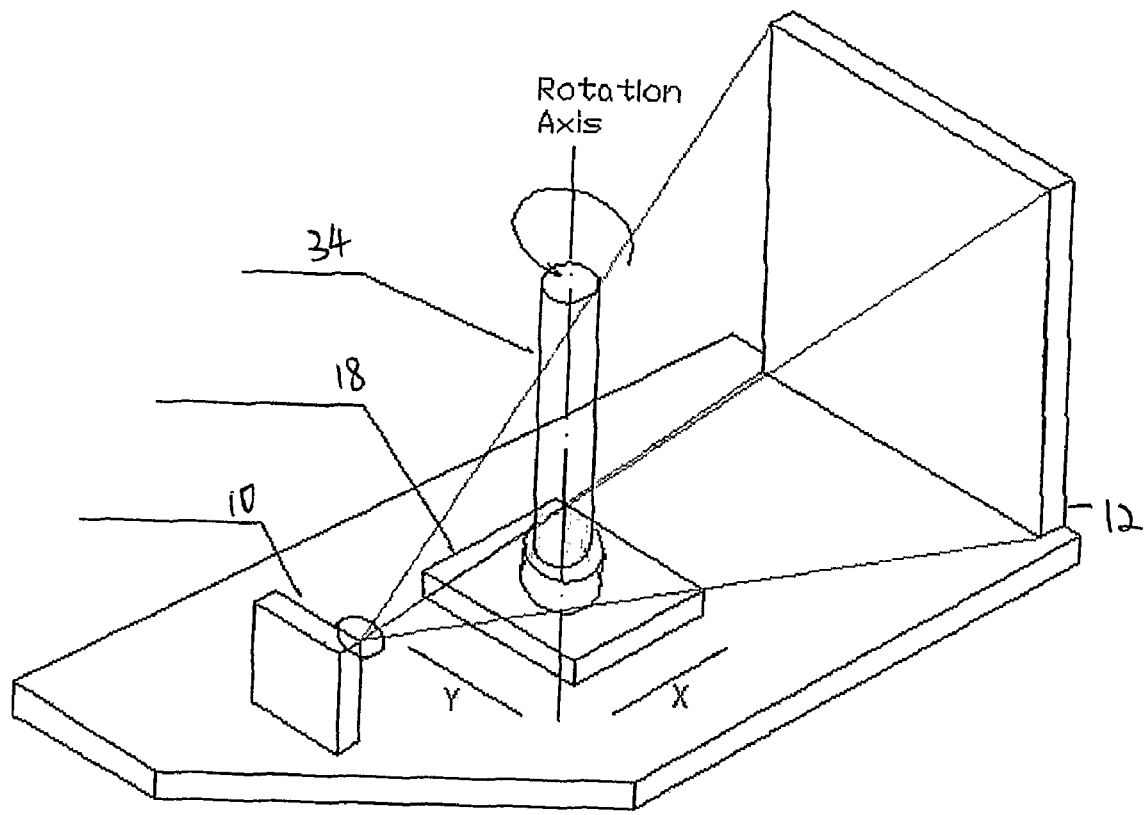
FIG. 3(a) is a schematic diagram of a prior art CT system using a wire phantom for central ray determination.

FIGS. 2 and 3(a) show a typical CT scan using such a prior art micro-CT system. Before the CT scan, the object 16 to be inspected is mounted on the rotator 18 and the best scan position for the object 16 is identified (201). The proper tube voltage and tube current for a good contrast of the image for all scan angles are selected. The object 16 is then calibration for offset (202), gain (203) and wedge (204) conducted. A wire phantom 34 is mounted (205). The wire phantom 34 is usually a straight wire fixed in a plastic tube. It is held by the rotator 18 and rotated for 360-degree at predetermined angle steps during which it is scanned for central ray 22 determination (206). The sinogram is then generated from all the inspections obtained at all angles and is used to determine the position of the central ray 22. If the central ray 22 is not successfully identified, a larger diameter wire phantom 34 is used until the central ray 22 is determined. After the successful determination of the central ray 22, the wire phantom 34 is removed and the object 16 to be inspected is again mounted on the rotator 18 (207). The corresponding CT scan parameters are set (208) and the CT scan commenced (209). With the inspection of the object 16 obtained, the cross-sectional image of the object 16 is reconstructed (240).

Figure 3B:
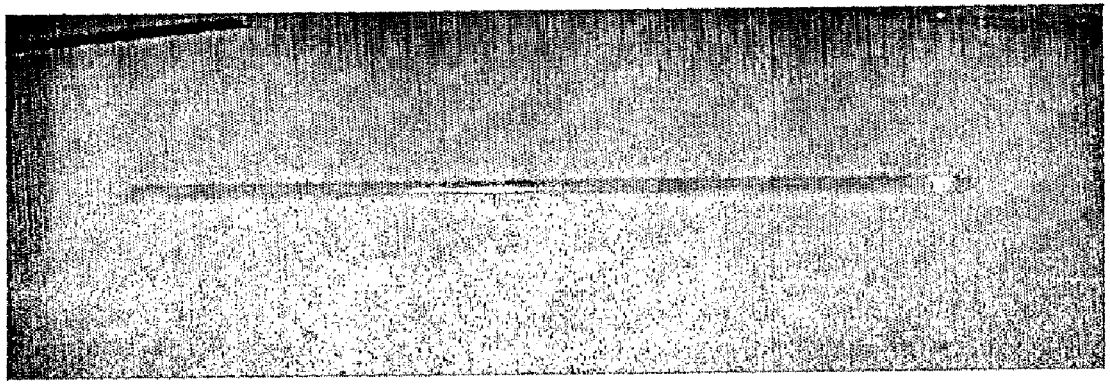
FIG. 3(b) is the photograph of a practical wire phantom used for central ray determination.
Figure 3C:
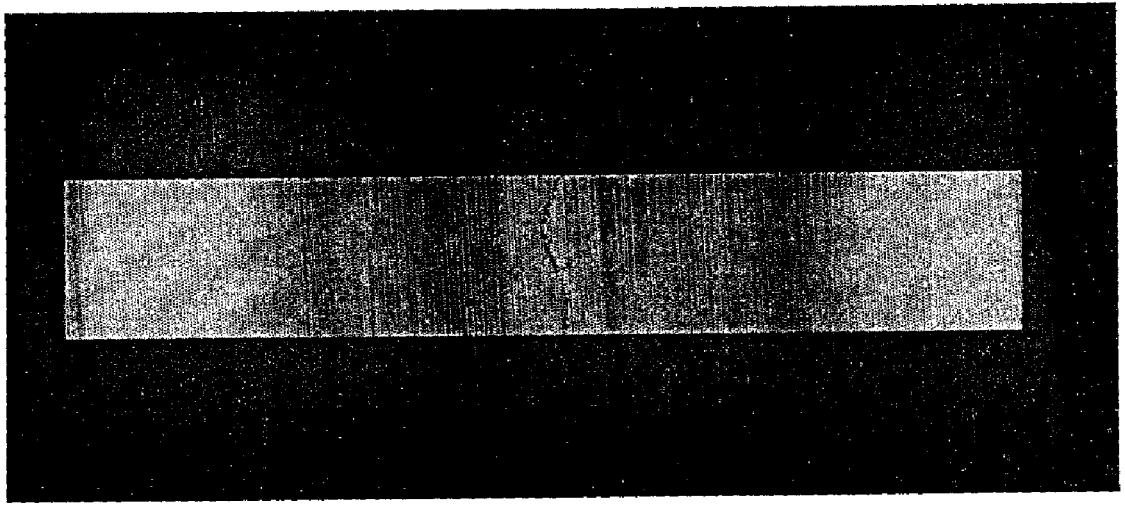
FIG. 3(c) is an example of a sinogram of a prior art phantom wire generated from its projections.

FIG. 3(b) shows a photo of a practical wire phantom and FIG. 3(c) is an example of the sinogram of a wire phantom generated from its inspections.

Figure 4A:
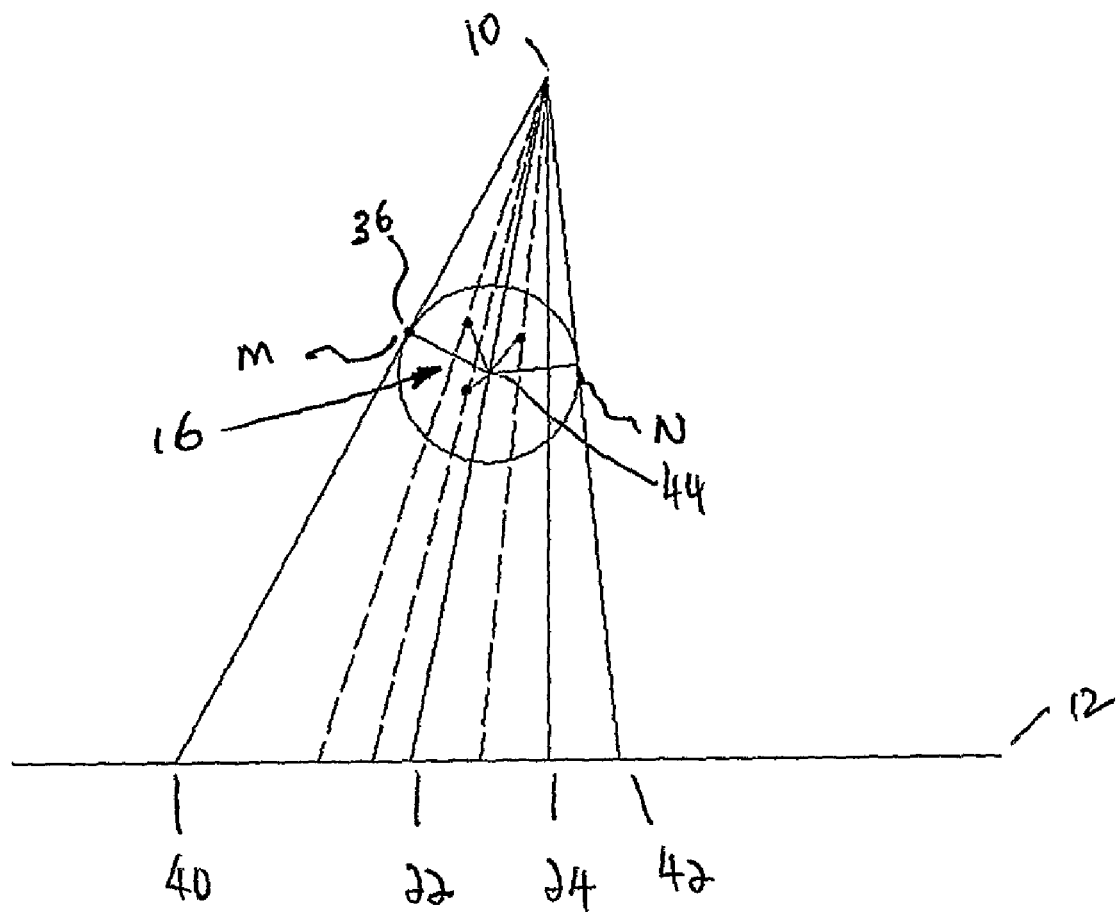
FIG. 4(a) illustrates a first preferred embodiment in which an object with several balls of different radius is used for a CT scan.

FIG. 4 illustrates the principle of the first embodiment in which an object 16 with four balls of different radius from the rotation axis 44 is used for a CT scan. With a scan of a complete circle, or an 180 degrees plus the fan beam angle arc, only the ball 36 with the largest radius generates the widest projection on the detector 12. That is, the left 40 and right 42 boundaries of the sinogram of a selected slice are from the largest-radius ball 36 in that slice of the object 16. Therefore, once the position of the rotation axis 44 is given, the included angle of:

the left tangential point M, where the beam that provides the leftmost point 40 creates a tangent with ball 36, the source 10, and the right tangential point N where the beam that provides the rightmost point 42 creates a tangent with ball 36 ("MSN")

is determined by using the radius of the largest-radius ball 36. By finding the corresponding scan angles of the left 40 and right 42 boundaries of the projection, the MSN angle can be determined. Because the central ray 22 must bisect the MSN angle, the angle for the central ray 22 is obtained. The left 40 and right 42 boundaries can be identified by use of a known edge detection algorithm. Additional methods such as curve fitting may be used to improve the accuracy to a sub-pixel level.

One method to determine the MSN angle is to make use of the known central channel 24 and the detector pixel size 26. As described before, the central channel 24 is defined as the ray perpendicular to the detector array. With a fixed X-ray source 10 and detector 12, the central channel 24 and detector pixel size 26 are always fixed and will not change unless the source 10 and/or detector 12 are moved. This may be due to, for example, replacing a damaged camera. Based on a known central channel C and detector pixel size p, the central ray can be calculated as following:

$$\overline{OC} = \left(\frac{\overline{SC}}{p}\right) * tg\left\{\left[tg^{-1}\left(\frac{\overline{LC}*p}{\overline{SC}}\right) - tg^{-1}\left(\frac{\overline{CR}*p}{\overline{SC}}\right)\right]/2\right\}$$

where $\overline{SC}$ is the source-to-detector distance (unit: μm); $\overline{OC}$, $\overline{LC}$, $\overline{RC}$ are the distances from the central ray point O, the left end of projection L and the right end of projection R to the central channel point C respectively (unit: pixel). All $\overline{SC}$, $\overline{OC}$, $\overline{LC}$, $\overline{RC}$ are vectors and their the signs are determined according to their relative positions to the central channel. For circumstances where $$tg^{-1}\left(\frac{\overline{LC}*p}{SC}\right) \approx \frac{\overline{LC}*p}{SC} \text{ and } tg^{-1}\left(\frac{\overline{CR}*p}{SC}\right) \approx \frac{\overline{CR}*p}{SC},$$

the above formula can be simplified as following $$\overline{OC} = \frac{1}{2}(\overline{LC} - \overline{CR}) = \frac{1}{2}(|LC| + |CR|)$$

With the central ray point O identified, the process of reconstruction can start.

Figure 4B:
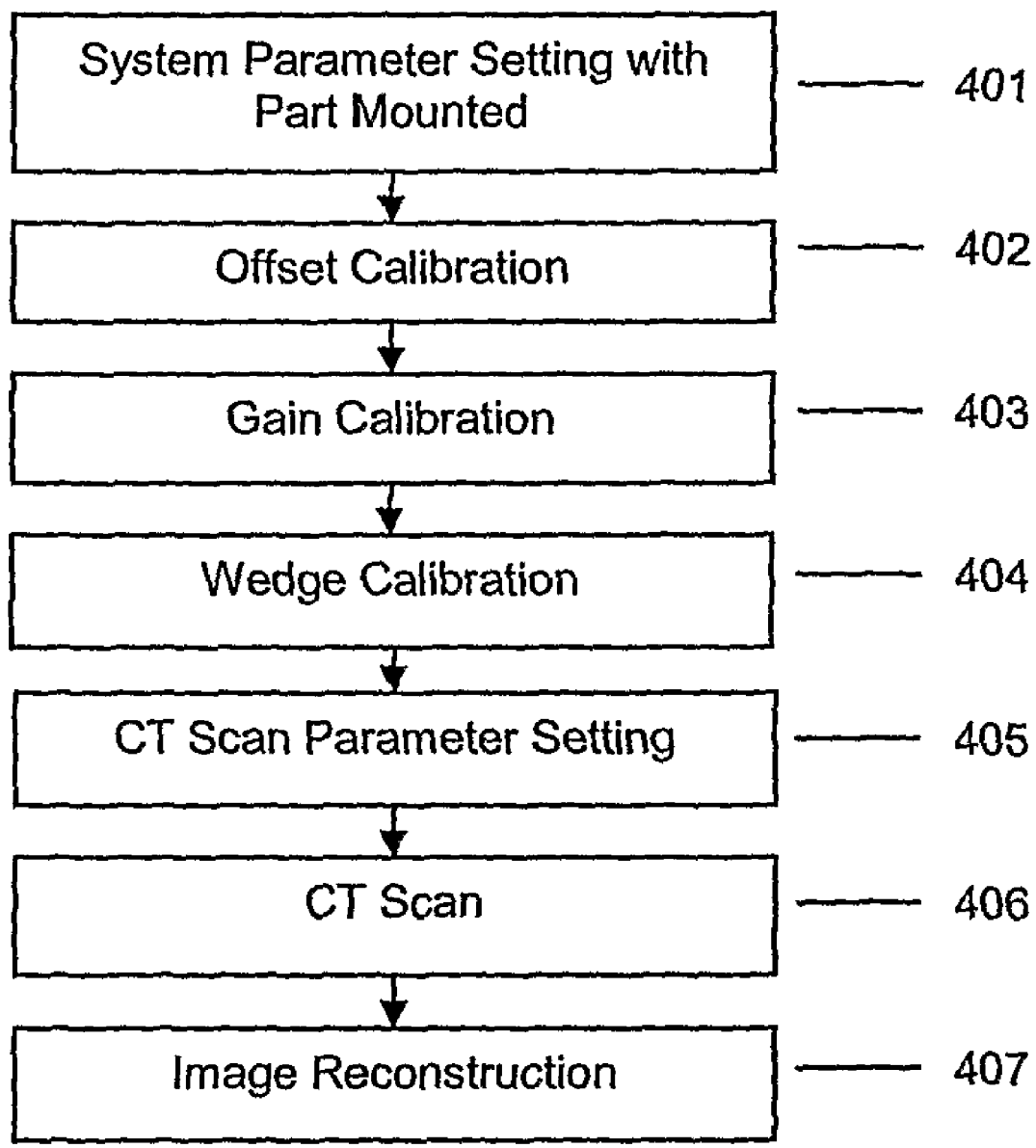
FIG. 4(b) is a flowchart of the CT scan process of the first preferred embodiment.

FIG. 4(b) is a flowchart of the CT scan. The object 16 is mounted and the parameters set (401). After shifting the manipulator with the object 16 sideways out of the radiation area, calibrations for offset (402), gain (403) and wedge (404) effects take place. With a stable X-ray source 10 and digital detector 12, this step can be conducted once a day and only needs to be repeated when the tube voltage or current is changed. The manipulator with the object 16 is shifted back to the previous position (405) on the rotator 18 and the scan (406) and reconstruction (407) take place.

Based on this CT scan, a one-step micro industry CT inspection system is possible that is simpler than previous systems, and enables the automatic performing of determining the system parameter settings, object positioning, offset calibration, gain calibration, wedge calibration, the CT scan, and image reconstruction. The automated system parameter setting may be by image analysis of the object under illumination, or checking a look-up table created for the relationship between the system parameters and the object's properties, including shape and size. Automated object positioning may be achieved by analyzing the image of the object under illumination.

Figure 5A:
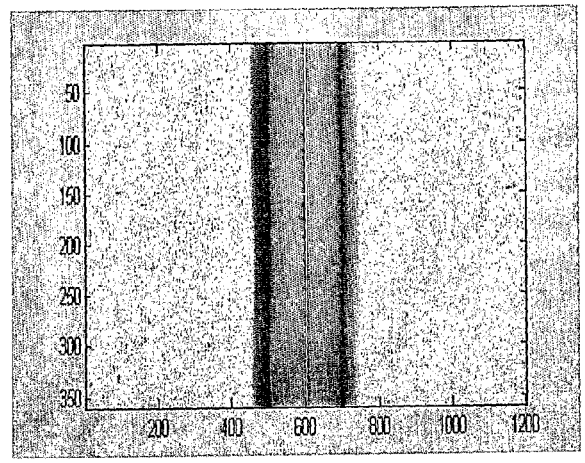
FIG. 5(a) shows the central ray of the first preferred embodiment determined with a wire phantom at a randomly chosen rotation axis at a distance to the central channel.

FIG. 5(a) shows the central ray 22 determined with a wire phantom 34 at a randomly chosen rotation axis. The wire phantom 34 is intentionally placed at a distance to the rotational axis to create a radius to the rotational axis.

Figure 5B:
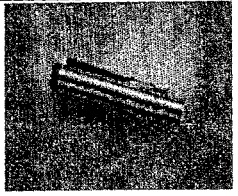
FIG. 5(b) shows the central ray directly determined with objects with big differences in both shape and materials, all objects being scanned at the same rotation axis as FIG. 5(a)
Figure 5B:
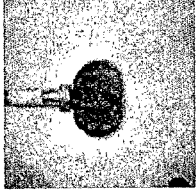
Figure 5B:
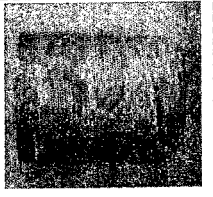
Figure 5B:

FIG. 5(b) summarizes the central rays determined with objects with differences in both shape and material. All objects were scanned at the same rotation axis as FIG. 5(a). The values of the central rays are properly determined using their own projection data. The variations agree with that observed with a wire phantom 34 through a repeatability study.

Figure 6:
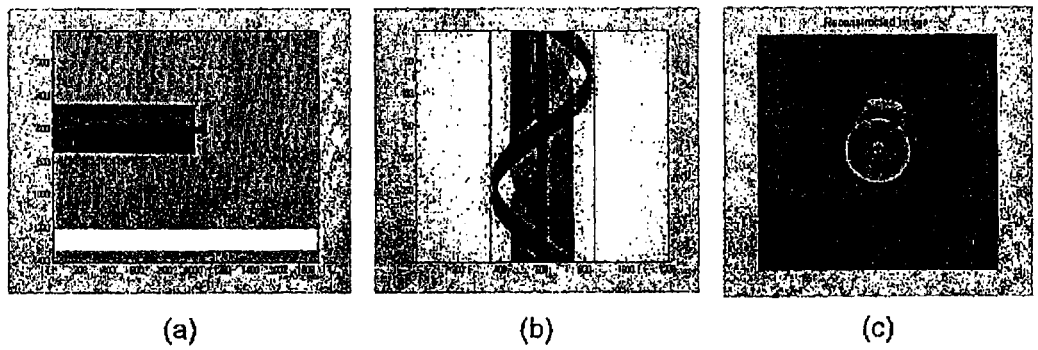
FIG. 6(a) is a demonstration with a pen-shaped diamond cutter cap.
FIG. 6(b) is a 2D projection of the object of FIG. 6(a)
FIG. 6(c) is a reconstructed image of the object of FIG. 6(a)

FIG. 6 is a demonstration with a pen-shaped diamond cutter cap. FIG. 6(a) is a 2D projection of the object; FIG. 6(b) is a sinogram of one slice with the left end and right end of the sinogram identified; and FIG. 6(c) is the reconstructed slice image of the object.

Figure 7:
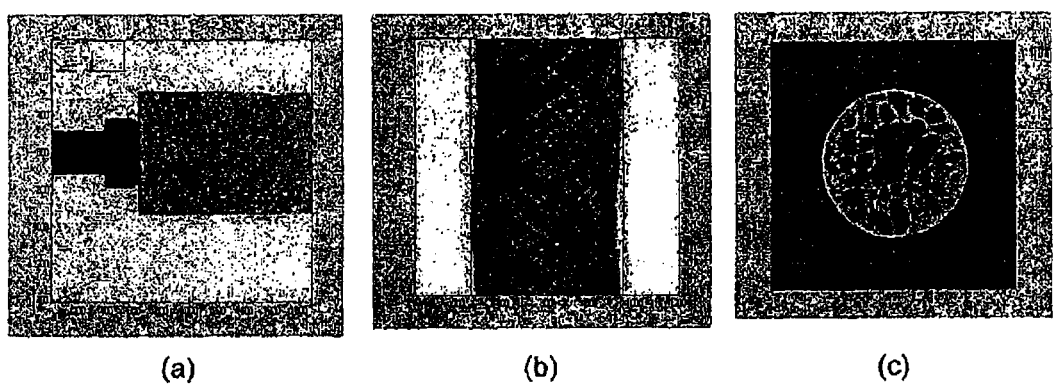
FIG. 7(a) is a demonstration with a carved ceramic owl.
FIG. 7(b) is a 2D projection of the object of FIG. 7(a)
FIG. 7(c) is a reconstructed image of the object of FIG. 7(a)

FIG. 7 is a demonstration with a carved ceramic owl. FIG. 7(a) is a 2D projection of the object; FIG. 7(b) is a sinogram of one slice with the left end and right end of sinogram identified; and FIG. 7(c) is the reconstructed slice image of the object.

Figure 8:
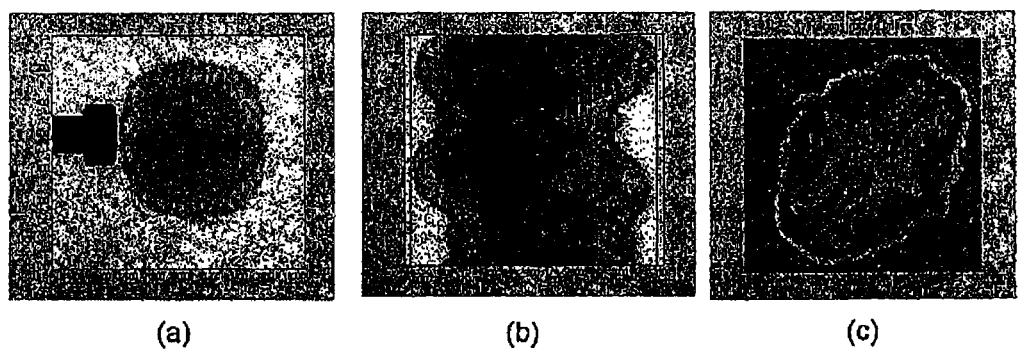
FIG. 8(a) is a demonstration with a walnut.
FIG. 8(b) is a 2D projection of the object of FIG. 8(a)
FIG. 8(c) is a reconstructed image of the object of FIG. 8(a)

FIG. 8 is a demonstration with a walnut. FIG. 8(a) is a 2D projection of the object; FIG. 8(b) is a sinogram of one slice with the left end and right end of sinogram identified; and FIG. 8(c) is the reconstructed slice image of the object.

Figure 9:
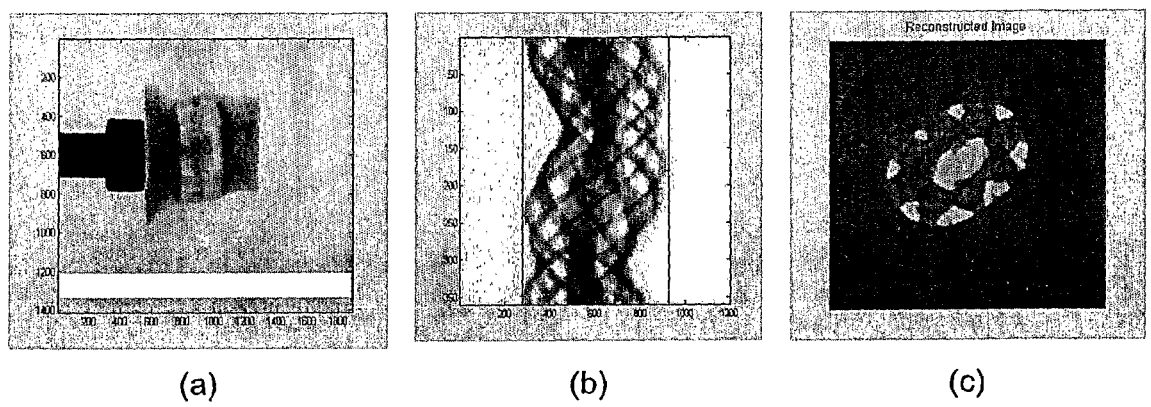
FIG. 9(a) is a demonstration with aluminum foam.
FIG. 9(b) is a 2D projection of the object of FIG. 9(a)
FIG. 9(c) is a reconstructed image of the object of FIG. 9(a)

FIG. 9 is the demonstration with aluminum foam. FIG. 9(a) is a 2D projection of the object; FIG. 9(b) is a sonogram of one slice with the left end and right end of sinogram identified; and FIG. 9(c) is the reconstructed slice image of the object.

Figure 10:
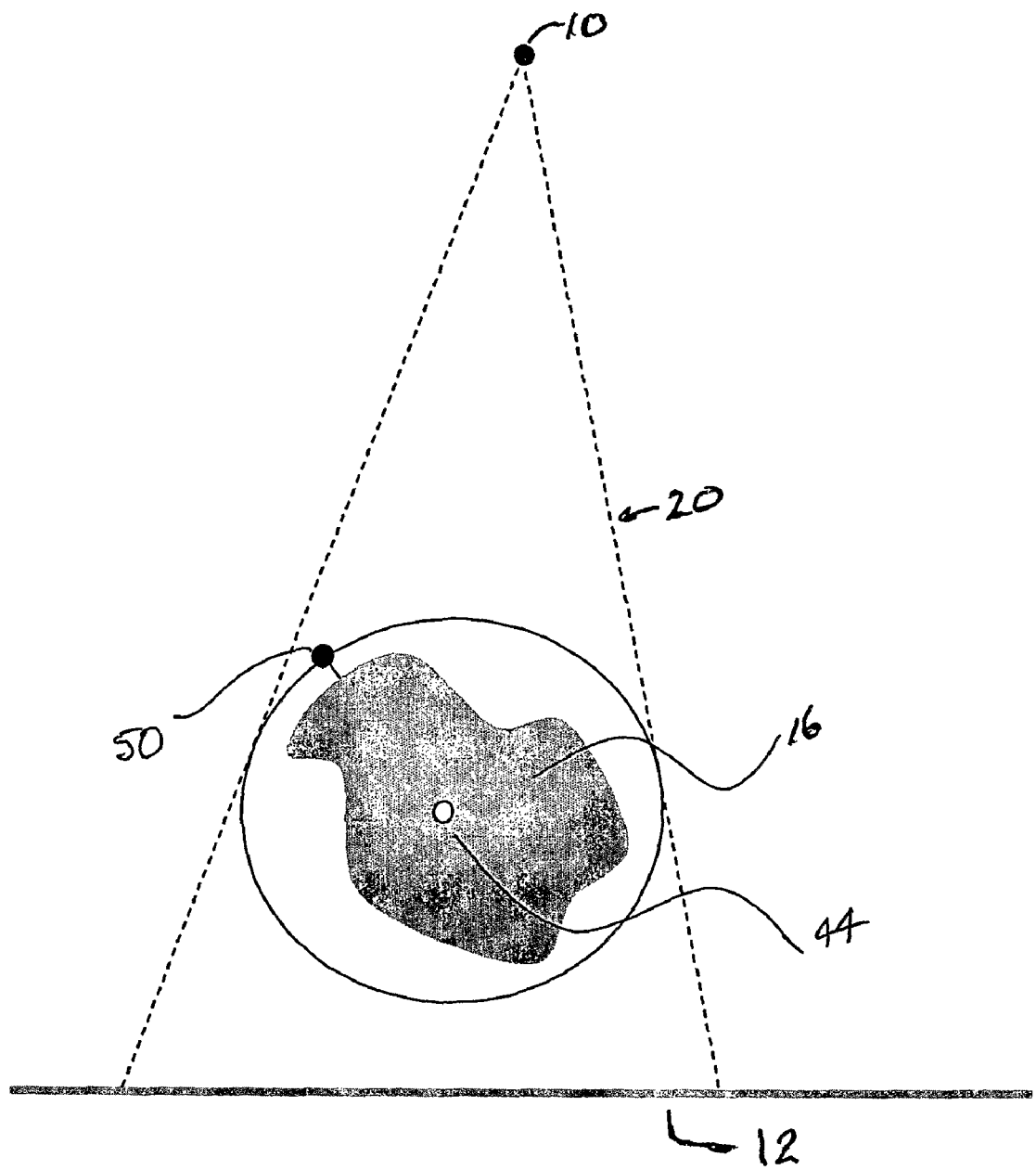
FIG. 10 is a view corresponding to FIG. 4(a) but of a second preferred embodiment.

FIG. 10 is a second embodiment in which a relatively small object 50 made of a dense material is adhered to the object 16 to be inspected, which has a special structure or material density distribution. The small object 50 may be placed at a non-interest area of the object 16 so that the areas of interest of the object 16 will not be affected. The CT scan can then be performed in the manner as described above. Because of the special structure or material property distribution of the object 16, it may not generate good projection contrast for proper boundary identification, the small object 50 is used to produce the necessary contrast.

Figure 11:
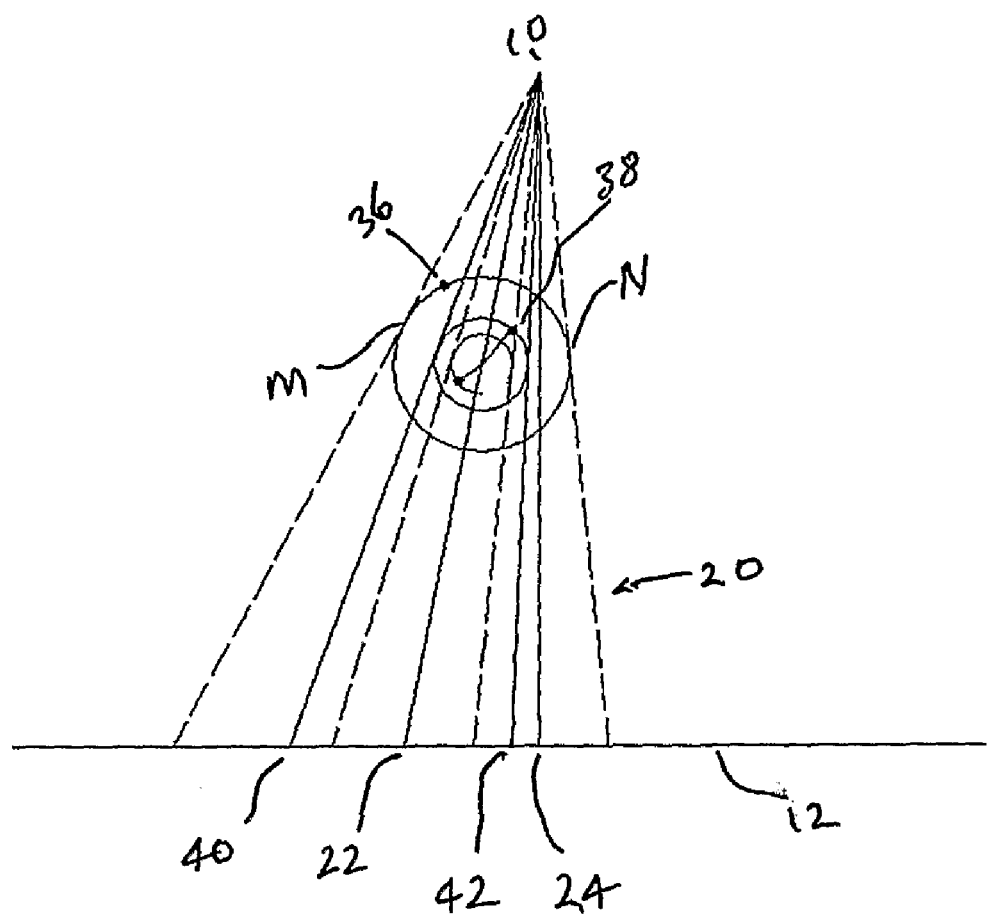
FIG. 11 is a view corresponding to FIG. 4(a) but of third preferred embodiment.

FIG. 11 shows a third embodiment with which the projection of the object point with largest radius 36 is not used. The projection of the point 38 which generates a contrast much clearer than its surrounding points is used for calculating the central ray 22.

The CT process is therefore simplified and more user-friendly. It is also possible to integrate all calibration processes into a CT scan process so automation is improved.

Whilst there has been described in the foregoing description preferred embodiments of the present invention, it will be understood by those skilled in the technology concerned that many variations or modifications in details of design or construction may be made without departing from the present invention.

The invention claimed is:

1. A computed tomography system comprising:
   (a) a fixed X-ray source for producing a fan beam;
   (b) a fixed digital detector; and
   (c) a manipulator for holding and rotating an object to be inspected; and wherein the computed tomography system is configured to use left and right projections of the rotated object on the fixed digital detector to determine a central ray position, and to reconstruct an image of the object being based on the central ray position.

2. The system as claimed in claim 1, wherein the computed tomography system is configured to use a sinogram of the projections of the object to determine the central ray position.

3. A computed tomography system as claimed in claim 1, wherein the computed tomography system is configured to use an included angle to determine the central ray position, the included angle being between the left projection of the object, the fixed X-ray source, and the right projection of the object.

4. The system as claimed in claim 3, wherein the central ray bisects the included angle.

5. The system as claimed in claim 3, wherein the computed tomography system is configured to use a part of the object with a largest radius to an axis of rotation to determine the left and right projections of the object on the fixed digital detector, the left projection of the part being a leftmost projection and the right projection being the rightmost projection.

6. The system as claimed in claim 3, wherein the computed tomography system is configured to use a sinogram of the projections of the object to determine the central ray position, wherein the computed tomography system is configured to obtain a central channel and a pixel size of the detector; and the computed tomography system is configured to determine the central ray by identifying the left and right ends of the sinogram.

7. The system of claim 3, wherein the computed tomography system is configured to use left and right projections of a point of the object which generates a much clearer contrast to determine the central ray position.

8. The system as claimed in claim 7, wherein the point comprises a relatively small object made of a material more dense than that of the object; the relatively small object being attached to the object.

9. The system as claimed in claim 8, wherein the relatively small object is attached to the object remote from at least one area of interest of the object for enabling a reconstructed image quality to not be affected.

10. A computed tomography method comprising:
 (a) producing a fan beam of X-rays at a fixed X-ray source;
 (b) detecting the X-rays at a fixed digital detector;
 (c) rotating an object to be inspected using a manipulator;
 (d) determining left and right projections of the object on the fixed digital detector;
 (e) determining a central ray position from the left and right projections; and
 (f) reconstructing an image of the object using the central ray position.

11. The method as claimed in claim 10, wherein a sinogram of the projections of the object is used to determine the central ray position.

12. A method as claimed in claim 10, wherein an included angle is used to determine the central ray position, the included angle being between the left projection of the object, the fixed X-ray source, and the right projection of the object.

13. The method as claimed in claim 12, wherein the central ray bisects the included angle.

14. The method as claimed in claim 12, wherein a part of the object with a largest radius to an axis of rotation is used to determine the left and right projections of the object on the fixed digital detector; the left projection of the part being a leftmost projection, and the right projection of the part being the rightmost projection.

15. The method as claimed in claim 12, wherein a sinogram of the projections of the object is used to determine the central ray position, and wherein a central channel and a pixel size of the detector are known; the central ray being determined by identifying the left and right ends of the sinogram.

16. The method of claim 12, wherein the left and right projections of a point of the object which generates a clearer contrast are used to determine the central ray position.

17. The method as claimed in claim 16, wherein the point comprises a relatively small object made of a material more dense than that of the object; the relatively small object being attached to the object.

18. The method as claimed in claim 17, wherein the relatively small object is attached to the objection remote from areas of interest of the object for enabling a reconstructed image quality to not be affected.

* * * * *